(12) United States Patent
Hagstrom et al.

(10) Patent No.: US 7,435,723 B2
(45) Date of Patent: *Oct. 14, 2008

(54) PROCESS FOR DELIVERY OF POLYNUCLEOTIDES TO THE PROSTATE

(75) Inventors: James E. Hagstrom, Middleton, WI (US); Mark Noble, Monona, WI (US); Julia Hegge, Monona, WI (US); Vladimir G. Budker, Middleton, WI (US)

(73) Assignee: Mirus Bio Corporation, Madison, WI (US)

( * ) Notice: Subject to any disclaimer, the term of this patent is extended or adjusted under 35 U.S.C. 154(b) by 890 days.

This patent is subject to a terminal disclaimer.

(21) Appl. No.: 10/680,742

(22) Filed: Oct. 6, 2003

(65) Prior Publication Data

US 2004/0067907 A1    Apr. 8, 2004

Related U.S. Application Data

(60) Continuation-in-part of application No. 09/447,966, filed on Nov. 23, 1999, now Pat. No. 6,627,616, which is a continuation-in-part of application No. 09/391,260, filed on Sep. 7, 1999, now abandoned, which is a division of application No. 09/975,573, filed on Nov. 21, 1997, now Pat. No. 6,265,387.

(51) Int. Cl.
*A61K 48/00* (2006.01)
*A01N 63/00* (2006.01)

(52) U.S. Cl. ........................ 514/44; 424/93.2
(58) Field of Classification Search .................. 514/44; 424/93.2

See application file for complete search history.

(56) References Cited

U.S. PATENT DOCUMENTS

| | | | |
|---|---|---|---|
| 5,521,291 | A | 5/1996 | Curiel |
| 5,580,859 | A | 12/1996 | Felgner |
| 5,583,020 | A | 12/1996 | Sullivan |
| 5,698,531 | A | 12/1997 | Nabel et al. |
| 5,922,687 | A | 7/1999 | Mann |
| 2004/0023850 | A1* | 2/2004 | Wolff et al. ............. 514/2 |
| 2005/0153451 | A1* | 7/2005 | Wolff et al. ............. 435/459 |

OTHER PUBLICATIONS

Parekh-Olmedo H, Gene therapy progress and prospects: targeted gene repair, 2005, Gene Therapy, vol. 12, pp. 639-646.*
Verma IM, Gene Therapy: Twenty-first century medicine, 2005, Annu. Rev. Biochem. vol. 74, pp. 711-738.*
Concalves M, A concise peer into the background, initial thoughts, and practices of human gene therapy, 2005, BioEssays, vol. 27, pp. 506-517.*
Zhu N, Systemic gene expression after intravenous DNA delivery into adult mice, 1993, Science, vol. 261, pp. 209-211.*

Acsadi G et al. "Direct gene transfer and expression into rat heart in vivo." The New Biologist 1991 vol. 3, No. 1, pp. 71-81.
Barron LG et al., "Cationic Lipids Are Essential For Gene Delivery Mediated By Intravenous Administration of Lipoplexes." Gene Therapy 1999 vol. 6 pp. 1179-1183.
Bohm W et al., "Routes of Plasmid DNA Vaccination That Prime Murine Humoral and Cellular Immune Responses." Vaccine 1998; vol. 16, No. 9/10; pp. 949-954.
Budker V et al., "Naked DNA Delivered Intraportally Expresses Efficiently in Hepatocytes." Gene Therapy 1996; vol. 3 pp. 593-598.
Budker V et al., "The Efficient Expression of Intravascularly Delivered DNA in Rat Muscle." Gene Therapy 1998 vol. 5 pp. 272-276.
Chapman G et al. "Gene transfer into coronary arteries of intact animals with a percutaneous balloon catheter," Circ. Res; 1992 vol. 71 pp. 27-33.
Coll JL et al. "In Vivo Delivery to Tumors of DNA Complexed With Linear Polyethylenimine." Human Gene Therapy 1999 vol. 10 pp. 1659-1666.
Goula, D. Et al., "Polyethylenimine-Based Intravenous Delivery of Transgene to Mouse Lung." Gene Therapy 1998/5; pp. 1291-1295.
Greelish JP et al. "Stable restoration of the sarcoglycan complex in dystrophic muscle perfused with histamine and a recombinant adeno-associated viral vector." Nature; 1999 vol. 5 No. 4 pp. 439-443.
Hickman MA et al. "Gene expression following direct injection of DNA into liver," Hum Gene Ther; 1994 vol. 5, No. 12 pp. 1477-1483.
Hickman MA et al. "Gene expression following direct injection of DNA into liver," Hum Gene Ther; 1994 vol. 5, No. 12 pp. 1477-1483.
Kawabata, K. Et al., "The Fate of Plasmid DNA After Intravenous Injection in Mice: Involvement of Scavenger Receptors in Its Hepatic Uptake." Pharmaceutical Research 1995; vol. 12, No. 6; pp. 825-830.
Liu F et al. "Hydrodynamics-based transfection in animals by systemic administration of plasmid DNA," Gene Ther; 1999 vol. 6 pp. 1258-1266.
Liu Y et al. "Cationic Liposome-Mediated Intravenous Gene Delivery." J Biol Chem 1995 vol. 270 No. 42; pp. 24864-24870.
Malone RW et al. "Dexamethasone enhancement of gene expression after direct hepatic DNA injection," J Biol Chem; 1994 vol. 269, No. 47 pp. 29903-29907.
McLean JW et al., "Organ-Specific Endothelial Cell Uptake of Cationic Liposome-DNA Complexes in Mice." The American Physiological Society 1997; pp. H387-H404.
Meyer KB et al. "Intratracheal gene delivery to the mouse airway: characterization of plasmid DNA expression and pharmacokinetics," Gene Ther; 1995 vol. 2, No. 7 pp. 450-460.
Milas M et al. "Isolated limb perfusion in the sarcoma-bearing rat: a novel preclinical gene delivery system," Clin Cancer Res; 1997 vol. 3 No. 12 Pt. 1, pp. 2197-203.

(Continued)

*Primary Examiner*—Peter Paras, Jr.
*Assistant Examiner*—David A. Montanari
(74) *Attorney, Agent, or Firm*—Kirk Ekena; Mark K. Johnson

(57) ABSTRACT

Disclosed is a system for providing in vivo delivery of polynucleotides to mammalian prostate cells using an intravascular administration route. The polynucleotides are inserted in an injection solution into a mammalian vasculature. Insertion of the injection solution at an appropriate rate increases the volume of extravascular fluid in the tissue thereby facilitating delivery of the polynucleotide to the cell.

13 Claims, No Drawings

OTHER PUBLICATIONS

Riessen R et al. "Arterial gene transfer using pure DNA applied directly to a hydrogel-coated angioplasty balloon," Hum Gene Ther; 1993 vol. 4, No. 6 pp. 749-758.

Sikes ML et al. "In vivo gene transfer into rabbit thyroid follicular cells by direct DNA injection," Hum Gene Ther; 1994 vol. 5, No. 7 pp. 837-844.

Song YK et al., "Enhanced Gene Expression in Mouse Lung by Prolonging the Retention Time of Intravenously Injected Plasmid DNA." Gene Therapy 1998; 5; pp. 1531-1537.

Soriano P et al. "Targeted and nontargeted liposomes for in vivo transfer to rat liver cells of a plasmid containing the preproinsulin I gene," PNAS; 1983 vol. 80 pp. 7128-7131.

Vile RG et al. "In vitro and in vivo targeting of gene expression to melanoma cells," Cancer Res; 1993 vol. 53 pp. 962-967.

Von Der Leyen H et al., "A Pressure-Mediatated Nonviral Method For Efficient Arterial Gene and Oligonucleotide Transfer." Human Gene Therapy 1999 vol. 10 pp. 2355-2364.

Wolff JA et al. "Direct gene transfer into mouse muscle in vivo." Science 1990 vol. 247 pp. 1465-1468.

Zhang et al. "Efficient expression of naked dna delivered intraarterially to limb muscles of nonhuman primates," Human Gene Therapy 2001 vol. 12 No. 4 pp. 427-438.

Zhang G et al. "High Levels of Foreign Gene Expression in Hepatocytes after Tail Vein Injections of Naked Plasmid DNA," Human Gene Therapy 1999; vol. 10 pp. 1735-1737.

Zhang G et al., "Expression of Naked Plasmid DNA Injected Into the Afferent and Efferent Vessels of Rodent and Dog Livers." Human Gene Therapy 1997; vol. 8 pp. 1763-1772.

Zhu N et al., "Systemic Gene Expression After Intravenous DNA Delivery Into Adult Mice." Science 1993; vol. 261 pp. 209-211.

* cited by examiner

PROCESS FOR DELIVERY OF POLYNUCLEOTIDES TO THE PROSTATE

CROSS REFERENCE TO RELATED APPLICATIONS

This application is a Continuation-In-Part of U.S. Ser. No. 09/447,966 filed on Nov. 23, 1999 now U.S. Pat. No. 6,627,616 which is a Continuation-In-Part from nonprovisional application Ser. No. 09/391,260, filed Sep. 7, 1999 now abandoned which is a Divisional from nonprovisional application Ser. No. 09/975,573, filed on Nov. 21, 1997 issued as U.S. Pat. No. 6,265,387.

BACKGROUND OF THE INVENTION

A basic challenge for biotechnology is to develop approaches for delivering genetic information to cells in vivo. The purposeful delivery of genetic material to somatic cells for the purpose of treating disease or for biomedical investigation has been termed gene therapy. Gene therapy promises to be a significant advance in the treatment of infections as well as somatic and hereditary genetic diseases. To be successful, the polynucleotide must be delivered to a therapeutically significant percentage of the affected cells in a manner that is both efficient and safe. The delivered polynucleotide can then compensate for a missing endogenous gene, provide a beneficial function or block activity of a dominant negative endogenous gene or gene of an infectious organism. If genetic materials are appropriately delivered to a patient they can potentially enhance a patient's health and, in some instances, lead to a cure. Specifically, the development of methods for gene transfer into the prostate is attractive given that prostate cancer is a leading cause of morbidity and mortality in men and has a stronger hereditary component than any other type of cancer. Most prostate tumors arise from the secretory epithelial cells that line the lumenal surface of the prostatic ducts and acini. It has been recognized that gene therapy could offer a new tool in the battle against this cancer. Delivery of genes to prostate in animal models will also further biomedical research into the causes, mechanisms and potential treatments of enlarged prostate, prostate cancer and benign prostatic hyperplasia.

It was first observed that the in vivo injection of plasmid DNA into muscle enabled the expression of foreign genes in muscle cells near the point of injection [Wolff et al. 1990]. Since that report, several other studies have reported foreign gene expression following the direct injection of DNA into the parenchyma of other tissues. Transfection following direct injection has been observed for: cardiac muscle [Acsadi et al 1991], pig epidermis [Hengge et al. 1995], rabbit thyroid [Sikes et al. 1994], melanoma tumors [Vile et al. 1993], rat liver [Malone et al. 1994, Hickman 1994] lung by intratracheal injection [Meyer et al. 1995], and into arteries using a hydrogel-coated angioplasty balloon [Riessen et al. 1993, Chapman et al. 1992]. A number of other techniques have also been explored for delivery of polynucleotides to cells in mammals. These techniques include the "gene gun" method, electroporation, the use of viral vectors, and cationic liposome and polymer transfection reagents. However, each of these techniques suffer from delivery to too few cells and/or toxicity. For instance, cationic DNA-containing complexes are highly effective in vitro but generally have been of limited success in vivo because the complexes are typically too large and their positive charge has an adverse influence on biodistribution.

SUMMARY OF THE INVENTION

In a preferred embodiment, the present invention provides processes for in vivo delivery of polynucleotides to prostate cells in a mammal comprising: injecting a solution containing the polynucleotide into a vessel of the prostate, wherein the volume and rate of the injection results in increasing permeability of prostate vessels and increasing the volume of extravascular fluid in the target tissue to provide for delivery of the polynucleotides to cells such as prostate cells outside the vessel. Increasing vessel permeability and increasing the volume of extravascular fluid in the target tissue may further comprise blocking the flow of fluid through vessels into and/or out of a target tissue or area. The solution may contain a compound or compounds which may or may not associate with the polynucleotide and may aid in delivery.

In a preferred embodiment, an in vivo process is described for increasing the transit of polynucleotides out of a vessel and into the cells of the prostate comprising: rapidly injecting a sufficient volume of injection solution containing the polynucleotides into an afferent or efferent vessel supplying or draining the prostate, thus forcing fluid out of the vasculature into the extravascular space, thereby increasing the volume of extravascular fluid in the target tissue and delivering the polynucleotides to prostate cells. This process may further consist of impeding the flow of fluid into and/or out of the prostate target area, inserting into the vessel a molecule(s) that increases vascular permeability, or both. The injection solution may further contain a compound or compounds which may aid in delivery and may or may not associate with the polynucleotides. For injection into an artery, the target tissue is the tissue that the artery supplies with blood under normal physiological conditions. For injection into a vein, the target tissue is the tissue from which the vein drains blood under normal physiological conditions.

In a preferred embodiment, a process is described for delivering a polynucleotide to a mammalian prostate cell in vivo comprising: inserting the polynucleotide into an afferent or efferent vessel of the prostate while impeding or occluding fluid flow through one or more vessels of the prostate. The process includes impeding fluid flow into and away from the prostate through afferent and efferent vessels of the prostate. Fluid flow through a vessel may be occluded by clamping the vessel or by a balloon catheter placed within the vessel. The vessels are occluded for a period of time necessary to deliver the polynucleotide without causing ischemic damage to the tissue.

In a preferred embodiment, the permeability of a vessel to the passage of macromolecules may be increased by delivering to the mammal a compound which is known in the art to increase vessel permeability. Such compounds may be selected from the list comprising: histamine, vascular permeability factor, calcium channel blockers, beta-blockers, phorbol esters, ethylene-diaminetetraacetic acid, adenosine, papaverine, atropine, nifedipine, and hypertonic solutions.

In a preferred embodiment, the polynucleotide that is delivered can be in a complex with a compound wherein the complex can have a zeta potential or surface charge that is neutral, cationic or anionic. The compound may be selected from the list comprising: viral vectors, non-viral vectors, and transfection agents. Viral vectors may be selected from the list comprising: adenovirus, adeno-associated virus, immunodeficiency virus, retrovirus, and lentivirus. Non-viral vectors may be selected from the list comprising: proteins, polymers, synthetic polymers, detergents, amphipathic compounds, lipids, polyampholytes, membrane active compounds and combinations thereof.

In a preferred embodiment, the described processes can be used to deliver a polynucleotide to a prostate cell for the purpose of altering the endogenous properties of the cell. The polynucleotide may be delivered to a cell in order to produce a cellular change that is therapeutic. For example, the polynucleotide may be delivered to the mammalian cell for the treatment of a disease or infection. Alternatively, the polynucleotide may be delivered to the cell to facilitate pharmaceutical drug discovery, drug target validation or for research. The polynucleotide may contain a gene that encodes a protein, peptide or functional RNA. The polynucleotide itself may alter the expression of an endogenous gene or a gene from a virus or bacteria infecting the cell.

In a preferred embodiment, the process may be used to deliver a therapeutic polynucleotide to a prostate cell for the treatment of disease. The delivered polynucleotide can express a protein or peptide that compensates for an absent, non-functional or dysfunctional endogenous gene. The gene may be selected from the list comprising: anticancer genes, tumor suppressors, immune response enhancing genes, RNASEL, Macrophage-scavenger receptor 1 (MSR1), Androgen Receptor, Cytochrome P-450c17 (CYP17), Steroid-5-α-reductase type II (SRD5A2), Glutathione S-transferase (GSTP1), NKX3.1, Phosphatase and tensin homologue (PTEN), and Cyclin-dependent kinase inhibitor (CDKN1B). An expressed protein or peptide may be secreted or stay within the cell. The delivered polynucleotide can also suppress or inhibit or otherwise alter expression of an endogenous gene or gene product. A polynucleotide may also be delivered to a mammalian cell in vivo to modulate immune response to induce or enhance an immune reaction against cancerous or abnormal prostate cells. Multiple polynucleotides or polynucleotides containing more that one gene may be delivered using the described process. Polynucleotides can be delivered to a patient that has an emlarged prostate, prostate cancer or benign prostatic hyperplasia or is at risk of getting cancer or benign prostatic hyperplasia. The prostate cell may be selected from the group consisting of epithelial cells, exocrine cells, basal epithelial cells, luminal epithelial cells, secretory cells, neuroendocrine cells, stromal cells, stromal fibroblasts, smooth muscle cells, and prostatic stem cells Further objects, features, and advantages of the invention will be apparent from the following detailed description when taken in conjunction with the accompanying drawings.

DETAILED DESCRIPTION OF THE INVENTION

We describe an intravascular process for the delivery of polynucleotides to cells in the prostate. Efficient delivery is achieved by increasing permeability of vessels in or near the target tissue and increasing the volume of extravascular fluid in the target area. Vessel permeability and extravascular fluid volume is increased by one or more of the following: using a sufficient volume of an appropriate injection solution, injecting the solution at an appropriate rate, impeding fluid flow into and out of the target tissue during the process, and increasing permeability of the vessel walls.

For delivery to extravascular cells, the polynucleotide must cross the endothelial barrier and vessel wall. Many blood vessels contain natural pores or fenestrae which allow passage of nutrients, etc. However, in most tissues these pores are too small-about 4 nm diameter-to allow extravasation of many potentially therapeutic molecules, including polynucleotides. Using the described process, extravasation of fluid and molecules out of vessels and delivery to cells of the surrounding parenchyma is provided.

The described delivery system comprises administering the polynucleotide to the mammal by insertion of a solution containing the polynucleotide into the lumen of a vessel in the mammal, i.e., an intravascular administration route. Intravascular herein means within an internal tubular structure called a vessel that is within the body of a mammal. Within the lumen or cavity of the vessel, a bodily fluid flows to or from a body part. Vessels comprise: arteries, arterioles, capillaries, venules, sinusoids, and veins. Afferent vessels are directed towards the organ or tissue. Fluid flows towards an organ or tissue in afferent vessels under normal physiological conditions. Conversely, efferent vessels are directed away from an organ or tissue and fluid flows away from the organ or tissue in efferent vessels under normal physiological conditions. In the liver, the hepatic vein is an efferent blood vessel since it normally carries blood away from the liver into the inferior vena cava. Also in the liver, the portal vein and hepatic arteries are afferent blood vessels in relation to the liver since they normally carry blood towards the liver. In the prostate, the prostatic venous plexus (the prostatic vein), a tributary of the deep doral vein of the penis, is an efferent blood vessel since it normally carries blood away from the prostate into the internal iliac vein. Another efferent vessel of the prostate is the vesical venous plexus, which is connected with the prostatic venous plexus. Also in the prostate, the inferior vesical (prostatic) artery is an afferent blood vessel in relation to the prostate since it normally carries blood towards the prostate. Arteries delivering blood to the prostate are derived from the internal pudic, hemorrhoidal (rectal) and internal iliac arteries. A vascular network consists of the directly connecting vessels supplying and/or draining fluid in a target organ or tissue.

A needle, catheter, or similar device is used to inject a solution containing the polynucleotide into a particular vessel. The vessel is chosen by selecting an afferent or efferent vessel of the target tissue. The injection can be performed under direct observation following incision and visualization of the vessel(s). The injection can also be performed without forming an incision using a needle that traverses the skin of the mammal and enters the lumen of a vessel. Alternatively, a catheter can be inserted at a distant site and threaded through a vessel(s) such that the instillation port of the catheter resides in a vessel that more directly connects with the target tissue. For example, the inferior vesical artery may be reached via the internal iliac artery or another blood vessel that ultimately connects to the inferior vesical artery. Balloon catheters allow for occlusion of the vessel as well as insertion of a solution into the vessel. The instillation port of a balloon catheter is located between the balloon and the target tissue. The injection solution can be injected into either an afferent vessel or an efferent vessel of the target tissue. For efferent vessels, distal is defined as upstream relative to the normal direction of fluid flow (i.e. the direction of increased branching, or toward the capillaries for blood vessels). For efferent vessels, proximal is defined as downstream relative to the normal direction of fluid flow. For afferent vessels, distal is defined as downstream relative to the normal direction of fluid flow (i.e. the direction of increased branching, or toward the capillaries for blood vessels). For afferent vessels, proximal is defined as upstream relative to the normal direction of fluid flow.

The present invention provides a process for inserting a solution containing a polynucleotide into the lumen of a vessel and delivering the polynucleotide to an extravascular cell in the prostate. Extravascular means outside of a vessel such as a blood vessel. Extravascular space means an area outside of a vessel. The extravascular space may contain biological matter such as cells and does not imply empty space. Extravasation of a polynucleotide means the movement of the polynucleotide out of the vessel into which it is introduced and into a parenchymal tissue or body cavity.

Efficient delivery via intravascular administration primarily depends on the volume of the injection solution and the injection rate. Vessel occlusion is also an important factor for delivery to many tissues. The use of hypertonic or hypotonic injection solutions or the use of vasodilators in the injection solution may further enhance delivery. The efficacy of polynucleotide delivery is also affected by the injection solution or the use of a transfection agent. For example, the use of low or no salt isotonic buffers can enhance the delivery of cationic polynucleotide-containing complexes.

Injecting into a vessel an appropriate volume at an appropriate rate increases permeability of the vessel to the injection solution and the molecules or complexes therein and increases the volume of extravascular fluid in the target tissue. Permeability of vessel walls and volume of extravascular fluid can be further increased by occluding outflow of fluid-both bodily fluid and injection solution-from the tissue or local vascular network. For example, a solution can be injected into an afferent vessel supplying an organ while afferent vessels(s) of the organ, efferent vessel(s) or the organ or both, are transiently occluded. Branching or collateral vessels or tributaries may also be occluded. Natural occlusions may be taken advantage of for impeding fluid outflow from the target vasculature. The vessel into which the solution is inserted may be occluded. If this vessel is occluded, the site of administration of the solution into the vessel is located between the occlusion and the target cells or tissue. The vessels are partially or totally occluded for a period of time sufficient to allow delivery of a molecule or complex present in the injection solution. The occlusion may be released immediately after injection or may be released only after a determined length of time which does not result in tissue damage due to ischemia.

Permeability of a vessel is defined herein as the propensity for macromolecules to move out of a vessel and enter the extravascular space. One measure of permeability is the rate at which macromolecules move through the vessel wall and out of the vessel. Another measure of permeability is the lack of force that resists the movement of fluid or macromolecules through the vessel wall and out of the vessel. Endothelial cells lining the interior of blood vessels and connective material (e.g., collagen) both functional to limit permeability of blood vessels to macromolecules.

The choice of injection volume and rate are dependent upon: the size of the animal, the size of the vessel into with the solution is injected, the size and or volume of the target tissue, the bed volume of the target tissue vasculature, and the nature of the target tissue or vessels supplying the target tissue. For example, delivery to liver may require less volume because of the porous nature of the liver vasculature. The precise volume and rate of injection into a particular vessel, for delivery to a particular target tissue, may be determined empirically. Larger injection volumes and/or higher injection rates are typically required for larger vessels, target sizes, etc. For example, efficient delivery to mouse liver may require injection of as little as 1 ml or less (animal weight ~25 g). In comparison, efficient delivery to dog or nonhuman primate limb muscle may require as much as 60-500 ml or more (animal weight 3-14 kg). Injection of 0.2 ml into clamped bladder to 2.3 ml into the tail vain (without clamps) results in delivery of polynucleotide to prostate in mouse. Injection rates can vary from 0.5 ml/sec or lower to 4 ml/sec or higher, depending on animal size, vessel size, etc. Occlusion of vessels, by balloon catheters, clamps, cuffs, natural occlusion, etc, can limit or define the vascular network size or target area.

The injection volume can be related to the target tissue. For example, delivery of a polynucleotide to a limb can be aided by injecting a volume greater than 5 ml per rat limb or greater than 70 ml for a primate limb. The injection volumes in terms of ml/limb muscle are usually within the range of 0.6 to 1.8 ml/g of muscle but can be greater. In another example, delivery of a polynucleotide to liver in mice can be aided by injecting the polynucleotide in an injection volume from 0.6 to 1.8 ml/g of liver or greater. In another example delivering a polynucleotide to a limb of a primate (rhesus monkey), the polynucleotide can be in an injection volume from 0.6 to 1.8 ml/g of limb muscle or anywhere within this range. In another example delivering a polynucleotide to mouse prostate, the polynucleotide can be in an injection volume from 0.1-1.5 ml.

In another embodiment the injection fluid is injected into a vessel rapidly. The rate or speed of the injection is partially dependent on the volume to be injected, the size of the vessel into which the volume is injected, and the size of the animal. In one embodiment the total injection volume (1-3 ml) can be injected from 5 to 15 seconds into the vascular system of mice. In another embodiment the total injection volume (6-35 ml) can be injected into the vascular system of rats from 20 to 7 seconds. In another embodiment the total injection volume (80-200 ml) can be injected into the vascular system of monkeys from 120 seconds or less.

The described intravascular delivery process requires that blood flow be impeded for substantially less time than is required to cause tissue damage by ischemia. In fact, a common anesthesia for human limb surgery (e.g., carpal tunnel repair) involves the blockage of blood flow for more than one hour. We have not observed any widespread histological evidence of ischemic damage in mice, rats, dogs, or primates following the described processes. The minimal elevations of indicator enzymes found in serum provide significant evidence against any consequential tissue damage.

These techniques may be combined with other agents known in the art for increasing vascular permeability, including drugs or chemicals and hypertonic solutions. Drugs or chemicals can increase the permeability of the vessel by causing a change in function, activity, or shape of cells within the vessel wall; typically interacting with a specific receptor, enzyme or protein of the vascular cell. Other agents can increase permeability by changing the extracellular connective material. Examples of drugs or chemicals that may be used to increase vessel permeability include histamine, vascular permeability factor (VPF, which is also known as vascular endothelial growth factor, VEGF), calcium channel blockers (e.g., verapamil, nicardipine, diltiazem), beta-blockers (e.g., lisinopril), phorbol esters (e.g., PKC), ethylenediaminetetraacetic acid (EDTA), adenosine, papaverine, atropine, and nifedipine. Hypertonic solutions have increased osmolarity compared to the osmolarity of blood thus increasing osmotic pressure and causing cells to shrink. Typically, hypertonic solutions containing salts such as NaCl or sugars or polyols such as mannitol are used.

Because tissue size, tissue vasculature and tissue vasculature fluid volume may not be identical from one individual to another, methods may be employed to predict or control appropriate injection volume and rate. Injection of iodinated contrast dye detected by fluoroscopy can aid in determining vascular bed size. Also, an automated injection system can be used such that the injection solution is delivered at a preset pressure or a preset injection rate. An injection system that allows for automated regulation of injection speed and volume correlated to the pressure in the injected vessel can be used. For example, an automated injection system can be used to inject the polynucleotide-containing solution such that a pressure threshold is reached and then maintained at or above this threshold for a given time. By creating a feedback between the pressure measured at a given site and the injection pump, a system can be created that automatically senses the target bed size and injects the proper volume of injection solution at an appropriate rate. For such a system, pressure may be measured in the injection apparatus, in the vessel into which the solution is injected, in a branch vessel within or near the target tissue, within an efferent or afferent vessel within or near the target tissue, or within the target tissue itself. For a given mammal, the volume and rate identified as effective for delivery to prostate in one individual can generally be considered to be effective for delivery to prostate in other individuals.

It is envisioned that the described processes may be used repetitively in a single mammal. Multiple injections may be used to provide delivery to additional tissues, to increase delivery to a single tissue, or where multiple treatments are indicated.

The described processes may be combined with other delivery vehicles or vectors or other delivery enhancing groups. Such delivery vehicles and groups comprise: transfection reagents, viral vectors, non-viral vectors, lipids, polymers, polycations, amphipathic compounds, targeting signals, nuclear targeting signals, and membrane active compounds.

Delivery of a nucleic acid means to transfer a nucleic acid from a container outside a mammal to near or within the outer cell membrane of a cell in the mammal. The term transfection is used herein, in general, as a substitute for the term delivery, or, more specifically, the transfer of a nucleic acid from directly outside a cell membrane to within the cell membrane.

A delivery system is the means by which a biologically active compound becomes delivered. That is all compounds, including the biologically active compound itself, that are required for delivery and all procedures required for delivery including the form (such as volume and phase (solid, liquid, or gas)) and method of administration.

The term polynucleotide, or nucleic acid or polynucleic acid, is a term of art that refers to a polymer containing at least two nucleotides. Nucleotides are the monomeric units of polynucleotide polymers. Polynucleotides with less than 120 monomeric units are often called oligonucleotides. Natural nucleic acids have a deoxyribose- or ribose-phosphate backbone. An artificial or synthetic polynucleotide is any polynucleotide that is polymerized in vitro or in a cell free system and contains the same or similar bases but may contain a backbone of a type other than the natural ribose-phosphate backbone. These backbones include: PNAs (peptide nucleic acids), phosphorothioates, phosphorodiamidates, morpholinos, and other variants of the phosphate backbone of native nucleic acids. Bases include purines and pyrimidines, which further include the natural compounds adenine, thymine, guanine, cytosine, uracil, inosine, and natural analogs. Synthetic derivatives of purines and pyrimidines include, but are not limited to, modifications which place new reactive groups such as, but not limited to, amines, alcohols, thiols, carboxylates, and alkylhalides. The term base encompasses any of the known base analogs of DNA and RNA. The term polynucleotide includes deoxyribonucleic acid (DNA) and ribonucleic acid (RNA) and combinations of DNA, RNA and other natural and synthetic nucleotides.

DNA may be in form of cDNA, in vitro polymerized DNA, plasmid DNA, parts of a plasmid DNA, genetic material derived from a virus, linear DNA, vectors (P1, PAC, BAC, YAC, artificial chromosomes), expression cassettes, chimeric sequences, recombinant DNA, chromosomal DNA, an oligonucleotide, anti-sense DNA, or derivatives of these groups. RNA may be in the form of oligonucleotide RNA, tRNA (transfer RNA), snRNA (small nuclear RNA), rRNA (ribosomal RNA), mRNA (messenger RNA), in vitro polymerized RNA, recombinant RNA, chimeric sequences, anti-sense RNA, siRNA (small interfering RNA), ribozymes, or derivatives of these groups. An anti-sense polynucleotide is a polynucleotide that interferes with the function of DNA and/or RNA. In addition, DNA and RNA may be single, double, triple, or quadruple stranded. Double, triple, and quadruple stranded polynucleotide may contain both RNA and DNA or other combinations of natural and/or synthetic nucleic acids.

Functional RNA: A functional RNA comprises any RNA that is not translated into protein but whose presence in the cell alters the endogenous properties of the cell. A RNA function inhibitor comprises any polynucleotide or nucleic acid analog containing a sequence whose presence or expression in a cell causes the degradation of or inhibits the function or translation of a specific cellular RNA, usually an mRNA, in a sequence-specific manner. Inhibition of RNA can thus effectively inhibit expression of a gene from which the RNA is transcribed. RNA function inhibitors are selected from the group comprising: siRNA, microRNA, interfering RNA or RNAi, dsRNA, RNA Polymerase II transcribed DNAs encoding siRNA or antisense genes, RNA Polymerase III transcribed DNAs encoding siRNA or antisense genes, ribozymes, and antisense nucleic acid, which may be RNA, DNA, or artificial nucleic acid. SiRNA comprises a double stranded structure typically containing 15-50 base pairs and preferably 21-25 base pairs and having a nucleotide sequence identical or nearly identical to an expressed target gene or RNA within the cell. An siRNA may be composed of two annealed polynucleotides or a single polynucleotide that forms a hairpin structure. Antisense RNAs comprise sequence that is complimentary to an mRNA. Antisense polynucleotides include, but are not limited to: morpholinos, 2'-O-methyl polynucleotides, DNA, RNA and the like. RNA polymerase III transcribed DNAs contain promoters selected from the list comprising: U6 promoters, H1 promoters, and tRNA promoters. RNA polymerase II promoters include U1, U2, U4, and U5 promoters, snRNA promoters, microRNA promoters, and mRNA promoters. These DNAs can be delivered to a cell wherein the DNA is transcribed to produce small hairpin siRNAs, separate sense and anti-sense strand linear siRNAs, or RNAs that can function as antisense RNA or ribozymes.

The RNA function inhibitor may be polymerized in vitro, recombinant RNA, contain chimeric sequences, or derivatives of these groups. The RNA function inhibitor may contain ribonucleotides, deoxyribonucleotides, synthetic nucleotides, or any suitable combination such that the target RNA and/or gene is inhibited. In addition, these forms of nucleic acid may be single, double, triple, or quadruple stranded.

A delivered polynucleotide can stay within the cytoplasm or nucleus apart from the endogenous genetic material. Alternatively, DNA can recombine with (become a part of) the endogenous genetic material. Recombination can cause DNA to be inserted into chromosomal DNA by either homologous or non-homologous recombination.

The polynucleotide can be a sequence whose presence or expression in a cell alters the expression or function of cellular genes or RNA. A polynucleotide can be delivered to a cell to express an exogenous nucleotide sequence, to inhibit, eliminate, augment, or alter expression of an endogenous nucleotide sequence, or to affect a specific physiological characteristic not associated with the cell prior to delivery of the polynucleotide. Polynucleotides may contain an expression cassette coded to express a whole or partial protein, or RNA.

A polynucleotide can be used to modify the genomic or extrachromosomal DNA sequences. This can be achieved by delivering a polynucleotide that is expressed. Alternatively, the polynucleotide can effect a change in the DNA or RNA sequence of the target cell. This can be achieved by hybridization, multistrand polynucleotide formation, homologous recombination, gene conversion, or other yet to be described mechanisms.

The term gene generally refers to a polynucleotide sequence that comprises coding sequences necessary for the production of a therapeutic polynucleotide (e.g., ribozyme) or a polypeptide or precursor. The polypeptide can be encoded by a full length coding sequence or by any portion of the coding sequence so long as the desired activity or functional properties (e.g., enzymatic activity, ligand binding, signal transduction) of the full-length polypeptide or fragment are retained. The term also encompasses the coding region of a gene and the including sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' untranslated sequences. The sequences that are located 3' or downstream of the coding region and which are present on the mRNA are referred to as 3' untranslated sequences. The term gene encompasses both cDNA and genomic forms of a gene. A genomic form or clone of a gene contains the coding region interrupted with non-coding sequences termed introns, intervening regions or intervening sequences. Introns are segments of a gene which are transcribed into nuclear RNA. Introns may contain regulatory elements such as enhancers. Introns are removed or spliced out from the nuclear or primary transcript; introns therefore are absent in the mature RNA transcript. The messenger RNA (mRNA) functions during translation to specify the sequence or order of amino acids in a nascent polypeptide. A gene may also includes other regions or sequences including, but not limited to, promoters, enhancers, transcription factor binding sites, polyadenylation signals, internal ribosome entry sites, silencers, insulating sequences, matrix attachment regions. These sequences may be present close to the coding region of the gene (within 10,000 nucleotides) or at distant sites (more than 10,000 nucleotides). These non-coding sequences influence the level or rate of transcription and/or translation of the gene. Covalent modification of a gene may influence the rate of transcription (e.g., methylation of genomic DNA), the stability of mRNA (e.g., length of the 3' polyadenosine tail), rate of translation (e.g., 5' cap), nucleic acid repair, nuclear transport, and immunogenicity. One example of covalent modification of nucleic acid involves the action of Label IT® reagents (Mirus Corporation, Madison, Wis.).

As used herein, the term gene expression refers to the process of converting genetic information encoded in a gene into RNA (e.g., small RNA, siRNA, mRNA, rRNA, tRNA, or snRNA) through transcription of a deoxyribonucleic gene (e.g., via the enzymatic action of an RNA polymerase), and for protein encoding genes, into protein through translation of mRNA. Gene expression can be regulated at many stages in the process. Up-regulation or activation refers to regulation that increases the production of gene expression products (i.e., RNA or protein), while down-regulation or repression refers to regulation that decrease production. Molecules (e.g., transcription factors) that are involved in up-regulation or down-regulation are often called activators and repressors, respectively.

The term expression cassette refers to a natural or recombinantly produced polynucleotide molecule that is capable of expressing a gene or genetic sequence. The term recombinant as used herein refers to a polynucleotide molecule that is comprised of segments of polynucleotide joined together by means of molecular biological techniques. The cassette contains the coding region of the gene of interest along with any other sequences that affect expression of the sequence of interest. An expression cassette typically includes a promoter (allowing transcription initiation), and a transcribed sequence. Optionally, the expression cassette may include transcriptional enhancers, non-coding sequences, splicing signals, transcription termination signals, and polyadenylation signals. An RNA expression cassette typically includes a translation initiation codon (allowing translation initiation), and a sequence encoding one or more proteins. Optionally, the expression cassette may include translation termination signals, a polyadenosine sequence, internal ribosome entry sites (IRES), and non-coding sequences. Optionally, the expression cassette may include a gene or partial gene sequence that is not translated into a protein. A nucleic acid can be used to modify the genomic or extrachromosomal DNA sequences. This can be achieved by delivering a nucleic acid that is expressed. Alternatively, the nucleic acid can effect a change in the DNA or RNA sequence of the target cell. This can be achieved by hybridization, multi-strand nucleic acid formation, homologous recombination, gene conversion, RNA interference or other yet to be described mechanisms.

The polynucleotide may contain sequences that do not serve a specific function in the target cell but are used in the generation of the polynucleotide. Such sequences include, but are not limited to, sequences required for replication or selection of the polynucleotide in a host organism.

Protein refers herein to a linear series of greater than two amino acid residues connected one to another as in a polypeptide. A therapeutic effect of the protein in attenuating or preventing the disease state can be accomplished by the protein either staying within the cell, remaining attached to the cell in the membrane, or being secreted and dissociated from the cell where it can enter the general circulation and blood. An expressed protein can cause a cancer cell to be less proliferative or cancerous (e.g., less metastatic), or interfere with the replication of a virus.

The delivered polynucleotide may encode a functional copy of a dysfunctional endogenous gene. Such a gene may be selected from the list comprising: RNASEL, Macrophage-scavenger receptor 1 (MSR1), Androgen Receptor, Cytochrome P-450c17 (CYP17), Steroid-5-α-reductase type II (SRD5A2), Glutathione S-transferase (GSTP1), NKX3.1, Phosphatase and tensin homologue (PTEN), and Cyclin-dependent kinase inhibitor (CDKN1B). The polynucleotide may also be delivered to inhibit expression or function of an endogenous gene or gene product. Genes which may be inhibited may be selected from the list comprising: Androgen Receptor, Cytochrome P-450c17 (CYP17), Steroid-5-α-reductase type II (SRD5A2), viral genes, and bacterial genes.

The transferred nucleic acid may encode an antigen which is expressed and induces a desired immune response. An antigen is defined as protein, subunit of a protein, or peptide that can serve as a target for an immune response. To induce an immune response, the nucleic acid may be delivered to a prostate cell, a prostate cancer cell or to another cell type. The expressed antigen may be secreted by the cell or be presented by the cell in the context of the major histocompatibility antigens, thereby eliciting an immune response. The method may be used to selectively elicit a humoral immune response (B cell mediated), a cellular immune response (T-cell mediated), or a mixture of these.

The immune response may result in the formation of antigen-specific antibodies, the induction of an antigen-specific cellular immune response, the induction of an antigen-specific T cell response of the induction of antigen-specific natural killer cells. The immune response may be directed against proteins associated with conditions, infections, diseases or disorders such as pathogen antigens or antigens associated with cancer cells.

A transfection agent or delivery vehicle is a compound or compounds that bind(s) to or complex(es) with oligonucleotides or polynucleotides (or peptides, proteins and small molecules), and mediates their entry into cells. Examples of transfection reagents include, but are not limited to, cationic liposomes and lipids, polyamines, calcium phosphate precipitates, histone proteins, polyethylenimine, polylysine, and polyampholyte complexes. It has been shown that cationic proteins like histones and protamines, or synthetic polymers like polylysine, polyarginine, polyornithine, DEAE dextran, polybrene, and polyethylenimine may be effective intracellular delivery agents. Typically, the transfection reagent has a component with a net positive charge that binds to the oligonucleotide's or polynucleotide's negative charge. The transfection reagent mediates binding of oligonucleotides and polynucleotides to cells via its positive charge (that binds to the cell membrane's negative charge) or via ligands that bind to receptors in the cell. For example, cationic liposomes or polylysine complexes have net positive charges that enable them to bind to DNA or RNA.

A transfection reagent may condense a polynucleotide. Condensing a polymer means decreasing the volume that the polymer occupies. An example of condensing nucleic acid is the condensation of DNA that occurs in cells. The DNA from a human cell is approximately one meter in length but is condensed to fit in a cell nucleus that has a diameter of approximately 10 microns. The cells condense (or compacts) DNA by a series of packaging mechanisms involving the histones and other chromosomal proteins to form nucleosomes and chromatin. The DNA within these structures is rendered partially resistant to nuclease DNase) action. The process of condensing polymers can be used for delivering them into cells of an organism.

Two molecules are combined to form a complex—through a process called complexation or complex formation—if they are in contact with one another through noncovalent interactions such as electrostatic interactions, hydrogen bonding interactions, and hydrophobic interactions. An interpolyelectrolyte complex is a noncovalent interaction between polyelectrolytes of opposite charge.

A polymer is a molecule built up by repetitive bonding together of two or more smaller units called monomers. The monomers can themselves be polymers. Polymers having fewer than 80 monomers are sometimes called oligomers. The polymer can be a homopolymer in which a single monomer is used or can be copolymer in which two or more monomers are used. The polymer can be linear, branched network, star, comb, or ladder types of polymer. Types of copolymers include alternating, random, block and graft.

The main chain of a polymer is composed of the atoms whose bonds are required for propagation of polymer length. For example in poly-L-lysine, the carbonyl carbon, α-carbon, and α-amine groups are required for the length of the polymer and are therefore main chain atoms. A side chain of a polymer is composed of the atoms whose bonds are not required for propagation of polymer length. For example in poly-L-lysine, the β, γ, δ, and ε-carbons, and ε-nitrogen are not required for the propagation of the polymer and are therefore side chain atoms.

To those skilled in the art of polymerization, there are several categories of polymerization processes that can be utilized in the described process. The polymerization can be chain or step. This classification description is more often used than the previous terminology of addition and condensation polymerization. Template polymerization can be used to form polymers from daughter polymers.

Step Polymerization: In step polymerization, the polymerization occurs in a stepwise fashion. Polymer growth occurs by reaction between monomers, oligomers and polymers. No initiator is needed since the same reaction occurs throughout and there is no termination step so that the end groups are still reactive. The polymerization rate decreases as the functional groups are consumed.

Chain Polymerization: In chain-reaction polymerization growth of the polymer occurs by successive addition of monomer units to limited numbers of growing chains. The initiation and propagation mechanisms are different and there is usually a chain-terminating step. The polymerization rate remains constant until the monomer is depleted.

A polyion (or polyelectrolyte), is a polymer possessing charge, i.e. the polymer contains a group (or groups) that has either gained or lost one or more electrons.

A polycation can be a polymer possessing net positive charge, for example poly-L-lysine hydrobromide or a histone. The polymeric polycation can contain monomer units that are charge positive, charge neutral, or charge negative, however, the net charge of the polymer must be positive. A polycation also can be a non-polymeric molecule that contains two or more positive charges.

A polyanion can be a polymer containing a net negative charge, for example polyglutamic acid. The polymeric polyanion can contain monomer units that are charge negative, charge neutral, or charge positive, however, the net charge on the polymer must be negative. A polyanion can also be a non-polymeric molecule that contains two or more negative charges.

The term polyion includes polycations, polyanions, zwitterionic polymers, and neutral polymers. The term zwitterionic refers to the product (salt) of the reaction between an acidic group and a basic group that are part of the same molecule. Salts are ionic compounds that dissociate into cations and anions when dissolved in solution. Salts increase the ionic strength of a solution, and consequently decrease interactions between nucleic acids with other cations. A charged polymer is a polymer that contains residues, monomers, groups, or parts with a positive or negative charge and whose net charge can be neutral, positive, or negative.

Polyampholytes are copolyelectrolytes containing both polycations and polyanions in the same polymer. In aqueous solutions polyampholytes are known to precipitate near the isoelectric point and form micelle-like structures (globules) at the excess of either charge. Such globules maintain tendency to bind other charged macromolecules and particles [Netz et al. 1998].

The polynucleotide itself, or a molecule that assists delivery or function of the polynucleotide (such as a transfection reagent) may contain a functional group. Functional groups include cell targeting signals, nuclear localization signals, compounds that enhance release of contents from endosomes or other intracellular vesicles (releasing signals), and other compounds that alter the behavior or interactions of the compound or complex to which they are attached.

Cell targeting signals are any signals that enhance the association of the biologically active compound with a cell. These signals can modify a biologically active compound such as drug or nucleic acid and can direct it to a cell location (such as tissue) or location in a cell (such as the nucleus) either in culture or in a whole organism. The signal may increase binding of the compound to the cell surface and/or its association with an intracellular compartment. By modifying the cellular or tissue location of the foreign gene, the function of the biologically active compound can be enhanced. The cell targeting signal can be, but is not limited to, a protein, peptide, lipid, steroid, sugar, carbohydrate, (non-expressing) polynucleic acid or synthetic compound. Cell targeting signals such as ligands enhance cellular binding to receptors. A variety of ligands have been used to target drugs and genes to cells and to specific cellular receptors. The ligand may seek a target within the cell membrane, on the cell membrane or near a cell. Binding of ligands to receptors typically initiates endocytosis. Proteins such as insulin, EGF, or transferrin can be used for targeting. Peptides that include the RGD sequence can be used to target many cells. Chemical groups that react with thiol, sulfhydryl, or disulfide groups on cells can also be used to target many types of cells. Folate and other vitamins can also be used for targeting. Other targeting groups include molecules that interact with membranes such as lipids, fatty acids, cholesterol, dansyl compounds, and amphotericin derivatives. In addition viral proteins could be used to bind cells.

After interaction of a compound or complex with the cell, other targeting groups can be used to increase the delivery of the biologically active compound to certain parts of the cell.

Nuclear localizing signals enhance the targeting of the pharmaceutical into proximity of the nucleus and/or its entry into the nucleus during interphase of the cell cycle. Such nuclear transport signals can be a protein or a peptide such as the SV40 large T antigen NLS or the nucleoplasmin NLS. These nuclear localizing signals interact with a variety of nuclear transport factors such as the NLS receptor (karyopherin alpha) which then interacts with karyopherin beta. The nuclear transport proteins themselves could also function as NLS's since they are targeted to the nuclear pore and nucleus. For example, karyopherin beta itself could target the DNA to the nuclear pore complex. Several peptides have been derived from the SV40 T antigen. Other NLS peptides have been derived from the hnRNP A1 protein, nucleoplasmin, c-myc, etc.

Delivery of a polynucleotide may be assisted by a membrane active compound. Compounds that disrupt membranes or promote membrane fusion are called membrane active compounds. These membrane active compounds, or releasing signals, enhance transport across the plasma membrane of a cell or enhance release of endocytosed material from intracellular compartments such as endosomes (early and late), lysosomes, phagosomes, vesicle, endoplasmic reticulum, golgi apparatus, trans golgi network (TGN), and sarcoplasmic reticulum. Release includes movement out of an intracellular compartment into the cytoplasm or into an organelle such as the nucleus. Releasing signals include chemicals such as chloroquine, bafilomycin or Brefeldin A1 and the ER-retaining signal (KDEL sequence), viral components such as influenza virus hemagglutinin subunit HA-2 peptides and other types of amphipathic peptides. The control of when and where the membrane active compound is active is crucial to effective transport. If the membrane active agent is operative in a certain time and place it would facilitate the transport of the biologically active compound across the biological membrane. If the membrane active compound is too active or active at the wrong time, then no transport occurs or transport is associated with cell rupture and cell death. Nature has evolved various strategies to allow for membrane transport of biologically active compounds including membrane fusion and the use of membrane active compounds whose activity is modulated such that activity assists transport without toxicity. Many lipid-based transport formulations rely on membrane fusion and some membrane active peptides' activities are modulated by pH. In particular, viral coat proteins are often pH-sensitive, inactive at neutral or basic pH and active under the acidic conditions found in the endosome.

An interaction modifier changes the way that a molecule interacts with itself or other molecules relative to molecule containing no interaction modifier. The result of this modification is that self-interactions or interactions with other molecules are either increased or decreased. For example cell targeting signals are interaction modifiers which change the interaction between a molecule and a cell or cellular component. Polyethylene glycol is an interaction modifier that decreases interactions between molecules and themselves and with other molecules. Dimethyl maleic anhydride modification or carboxy dimethylmaleic anhydride modification are other examples of interaction modifiers. Such groups can be useful in limiting interactions such as between serum factors and the molecule or complex to be delivered. They may also reversibly inhibit or mask an activity or function of a compound.

Parenchymal cells are the distinguishing cells of a gland, organ or tissue contained in and supported by the connective tissue framework. The parenchymal cells typically perform a function that is unique to the particular organ. The term "parenchymal" often excludes cells that are common to many organs and tissues such as fibroblasts and endothelial cells within the blood vessels.

In the prostate, the parenchyma include epithelial cells, exocrine cells, basal epithelial cells, luminal epithelial cells, secretory cells, neuroendocrine cells, stromal cells, stromal fibroblasts, smooth muscle cells, and prostatic stem cells.

A salt is any compound containing ionic bonds, (i.e., bonds in which one or more electrons are transferred completely from one atom to another). Salts are ionic compounds that dissociate into cations and anions when dissolved in solution and thus increase the ionic strength of a solution. Pharmaceutically acceptable salt means both acid and base addition salts.

Pharmaceutically acceptable acid addition salts are those salts which retain the biological effectiveness and properties of the free bases, and are not biologically or otherwise undesirable, and which are formed with inorganic acids such as hydrochloric acid, hydrobromic acid, sulfuric acid, nitric acid, phosphoric acid and the like, and organic acids such as acetic acid, propionic acid, pyruvic acid, maleic acid, malonic acid, succinic acid, fumaric acid, tartaric acid, citric acid, benzoic acid, mandelic acid, methanesulfonic acid, ethansulfonic acid, p-toluenesulfonic acid, salicylic acid, trifluoroacetic acid, and the like. Pharmaceutically acceptable base addition salts are those salts which retain the biological effectiveness and properties of the free acids, and are not biologically or otherwise undesirable. The salts are prepared from the addition of an inorganic base or an organic base to the free acid. Salts derived from inorganic bases include, but are not limited to, sodium, potassium, calcium, lithium, ammonium, magnesium, zinc, and aluminum salts and the like. Salts derived from organic bases include, but are not limited to salts of primary secondary, and tertiary amines, such as methylamine, triethylamine, and the like.

Analysis of expression of a reporter gene, or inhibition of a reporter gene, provides a reasonable expectation, accepted in the art, of the expression one can expect from delivery of other genes, such as therapeutic polynucleotides. Reporter gene/protein systems include:

Intracellular gene products such as luciferase, β-galactosidase, or chloramphenicol acetyl transferase. Typically, these are enzymes whose enzymatic activity can be easily measured.

Intracellular gene products such as β-galactosidase or green fluorescent protein which identify cells expressing the reporter gene. On the basis of the intensity of cellular staining, these reporter gene products also yield qualitative information concerning the amount of foreign protein produced per cell.

Secreted gene products such as growth hormone, factor IX, secreted alkaline phosphatase, or alpha1-antitrypsin. These proteins are useful for determining the amount of a secreted protein that a gene transfer procedure can produce. The reporter gene product can be assayed in a small amount of blood.

Measurement of inhibition of such genes can also be used in the analysis of delivery efficiency of interfering polynucleotides.

EXAMPLES

1. Delivery of a polynucleotide-containing complex to prostate in mouse via injection into the dorsal vein of the penis.

A. Synthesis of L-cystine-1,4-bis(3-aminopropyl)piperazine copolymer (M66): To a solution of N,N'-Bis(t-BOC)-L-cystine (85 mg, 0.15 mmol) in ethyl acetate (20 ml) was added N,N'-dicyclohexylcarbodiimide (108 mg, 0.5 mmol) and N-hyroxysuccinimide (60 mg, 0.5 mmol). After 2 h, the solution was filtered through a cotton plug and 1,4-bis(3-aminopropyl)piperazine (54 µL, 0.25 mmol) was added. The reaction was allowed to stir at room temperature for 16 h. The ethyl acetate was then removed by rotary evaporation and the resulting solid was dissolved in trifluoroacetic acid (9.5 ml), water (0.5 ml) and triisopropylsilane (0.5 ml). After 2 h, the trifluoroacetic acid was removed by rotary evaporation and the aqueous solution was dialyzed in a 15,000 MW cutoff tubing against water (2×2 L) for 24 h. The solution was then removed from dialysis tubing, filtered through 5 µm nylon syringe filter and then dried by lyophilization to yield 30 mg of polymer.

B. Formation of labile disulfide-containing polycation polymer/DNA complexes: 10 µg Plasmid DNA pCILuc and polymer M66 were mixed at a 1:1.7 wt:wt ratio in water and diluted to final volume with Ringer's.

C. Injection of complexes into dorsal vein of the prostate in mice: Animals were anesthetized with 1-2% isoflurane and a midline incision was made extending from the pubis to the mid-abdomen. Retractors were positioned to expose the bladder and male reproductive organs. In experiment #1, microvessel clamps were applied to the inferior vena cava and the anastomotic veins of the prostate just prior to injecting the polynucleotide. The polynucleotide-containing solution was injected into the dorsal vein of the penis in <7 sec. The injection volumes were 1.5 ml for experiment #1 and 2.3 ml for experiment #2. Clamps were removed 5-10 sec after the injection. Mice were sacrificed 24 hours after injection and various organs were assayed for luciferase expression. Luciferase activity is expressed as total relative light units per organ. The procedure resulted in high level reporter gene expression in the prostate.

TABLE 1a

Experiment #1, with clamps

| Organ | Luciferase Activity |
|---|---|
| Prostate | 129,982,450 |
| Testis | 4,229,000 |
| fat (around bladder) | 730,300 |
| bladder | 618,000 |

TABLE 1b

Experiment #2, without clamps

| Organ | Luciferase Activity |
|---|---|
| Prostate | 637,000 |
| Skin (abdominal wall) | 194,000 |
| Testis | 589,000 |
| Skeletal Muscle (quadriceps) | 35,000 |
| fat (peritoneal cavity) | 44,700 |
| bladder | 17,000 |
| pancreas | 2,520,000 |

2. Intravascular delivery of polynucleotides to the prostate.

A. Injection into bladder: ICR mice were anesthetized with 1-2% isoflurane and a midline incision was made extending from the pubis to the mid-abdomen. Retractors were positioned to expose the bladder and male reproductive organs. Curved vascular clamps were placed on the base of the bladder and the base of the seminal vesicles. Micro vascular clamps were also placed on the right and left ureters, the right and left deferent ducts and the urethral opening. A 30-gauge blunt needle catheter was inserted into the base of the bladder below the vascular clamp. The catheter was connected to a syringe pump and 20 µg pMIR48 plasmid DNA in 500 µl ringers was injected at a rate of 3 ml/min. Two min after injection the catheter was removed and the needle hole sealed with a hemostatic sponge. All clamps were removed and the abdominal wall was closed in two layers with 4-0 suture. Alternatively, the solution was injected directly into the prostate, 500 µl at 3 ml/min. The direct injection was performed using the same procedure as the bladder injections, including clamps, except that the solution was injected directly into the prostate. 24 h after injection, organs were harvested in the indicated volume of lysis buffer and 10 µl was assayed for luciferase activity.

B. Injection into tail vein: Tail vein injections of ~1.0 mL per 10 g body weight were preformed on ICR mice (n=2) using a 30 gauge, 0.5 inch needle. The injection solution contained 20 µg pMIR48 plasmid DNA in Ringer's. Injections were done manually with injection times of 4-5 sec [Zhang et al. 1999; Liu et al. 1999]. One day after injection, the prostates were harvested and homogenized in lysis buffer (0.1% Triton X-100, 0.1 M K-phosphate, 1 mM DTT, pH 7.8). Insoluble material was cleared by centrifugation and 10 µl of the cellular extract or was analyzed for luciferase activity as previously reported [Wolff et al 1990].

C. Injection into penis vein: ICR mice were anesthetized with 1-2% isoflurane and a midline incision was made extending from the pubis to the mid-abdomen. Retractors were positioned to expose the bladder and male reproductive organs. 20 µg pMIR48 plasmid DNA in 2.3 ml Ringer's was injected by hand into the dorsal vein of the penis at a rate of 3 ml/min. Because no clamps were used in this experiment, and because of the presence of connecting veins, this injection is similar to injection into tail vein. 24 h after injection, organs were harvested in the indicated volume of lysis buffer and 10 µl was assayed for luciferase activity.

D. Injection of DNA complexes: Plasmid DNA was combined with histone and the lipid MC798 at a weight ratio of 1:3:1 to form cationic transfection complexes in a low salt isotonic glucose solution.

Animals were anesthetized with 1-2% isoflurane and a midline incision was made extending from the pubis to the mid-abdomen. Retractors were positioned to expose the bladder and male reproductive organs. Microvessel clamps were applied to the inferior vena cava and the anastomotic veins of the prostate just prior to injecting the polynucleotide. 200 µl of the polynucleotide-containing solution was injected into the dorsal vein of the penis in <7 sec. Clamps were removed 5-10 sec after the injection. Mice were sacrificed 24 hours after injection and various organs were assayed for luciferase expression. Luciferase activity is expressed as total relative light units per organ. The procedure resulted in high level reporter gene expression in the prostate.

TABLE 2

Delivery of polynucleotides to prostate

| vol injected (ml) | lysis vol (ml) | animal | RLUs |
|---|---|---|---|
| A. Injection into bladder with clamps | | | |
| 0.5 | 0.5 | 1 | 12,285 |
| | | 2 | 1,144,862 |
| | | 3 | 79,390 |
| | | average | 412,179 |
| B. Injection into tail vein | | | |
| 2.3 | 0.5 | 1 | 1,435 |
| C. Injection into penis vein | | | |
| 2.3 | 0.5 | 1 | 457,949 |
| | | 2 | 201,597 |
| | | average | 329,773 |
| D. H1 lipid derivative w/isotonic glucose - direct injection | | | |
| 0.2 | 0.5 | 1 | 412,879 |
| E. H1 lipid derivative w/isotonic glucose - penis vein | | | |
| 0.2 | 0.5 | 1 | 264,479 |
| | | 2 | 236,785 |
| | | average | 250,632 |

3. Delivery of polynucleotides to the prostate via injection into the bladder.

ICR mice were anesthetized with 1-2% isoflurane and a midline incision was made extending from the pubis to the mid-abdomen. Retractos were positioned to expose the bladder and male reproductive organs. Curved vascular clamps were placed on the base of the bladder and the base of the seminal vesicles. Micro vascular clamps were placed on the right and left ureters, the right and left deferent ducts and the urethral opening. A 30-gauge blunt needle catheter was inserter into the base of the bladder below the vascular clamp. The catheter was connected to a syringe pump and 50 µg pMIR48 (firefly luciferase)+10 µg pMIR122 (Renilla luciferase) plasmid DNAs in 250 µl 5% mannitol was injected at a rate of 3 ml/min. Two min after the injection the catheter was removed and the needle hole sealed with a hemostatic sponge. All clamps were removed and the abdominal wall was closed in two layers with 4-0 suture.

TABLE 3

Delivery of plasmid DNA to prostate via injection in bladder

| animal | firefly | Renilla |
|---|---|---|
| 1 | 1,938,750 | 1,069,640 |
| 2 | 244,970 | 330,150 |
| 3 | 97,880 | 234,960 |

4. Intravascular delivery of polynucleotides to the prostate.

A. Delivery via the bladder: ICR mice were anesthetized with 1-2% isoflurane and a midline incision was made extending from the pubis to the mid-abdomen. Retractors were positioned to expose the bladder and male reproductive organs. Curved vascular clamps were placed on the base of the bladder and the base of the seminal vesicles. Micro vascular clamps were also placed on the right and left ureters, the right and left deferent ducts and the urethral opening. A 30-gauge blunt needle catheter was inserted into the base of the bladder below the vascular clamp. The catheter was connected to a syringe pump and 100 µg pMIR116+100 µg pMIR122 plasmid DNAs in Ringer's was injected at a rate of 3 ml/min. For mouse #1, 250 µl volume was injected. For mice #2-4, 200 µl volume was injected. Two min after the injection the catheter was removed and the needle hole sealed with a hemostatic sponge. All clamps were removed and the abdominal wall was closed in two layers with 4-0 suture.

B. Injection into the dorsal vein of the penis: ICR mice were anesthetized with 1-2% islofluorane and a midline incision was made extending from the pubis to the mid-abdomen. Retractors were positioned to expose the bladder and male reproductive organs. Microvessel clamps were applied to the inferior vena cava and the anastomotic veins of the prostate just prior to injecting the polynucleotide. 100 µg pMIR116 (P. pyralis luciferase)+100 µg pMIR122 (Renilla Luciferase) plasmid DNAs in 400 µl Ringer's was injected into the dorsal vein of the penis by hand at a rate of 3 ml/min. Two min after the injection the clamps were removed and the needle hole sealed with a hemostatic sponge. All clamps were removed and the abdominal wall was closed in two layers with 4-0 suture.

TABLE 4

Intravascular delivery of plasmid DNA to prostate

| | P. pyralis | Renilla |
|---|---|---|
| injection into bladder with clamps | | |
| 1 | 498,045 | 1,784,410 |
| 2 | 251,835 | 787,770 |
| 3 | 77,835 | 364,210 |
| 4 | 76,740 | 396,875 |
| average | 226,114 | 833,316 |
| st. dev. | 199,087 | 662,620 |
| injection into penis vein | | |
| 5 | 81,480 | 306,260 |
| 6 | 38,675 | 143,260 |
| 7 | 17,450 | 161,810 |
| average | 45,868 | 203,777 |
| st. dev. | 32,615 | 89,236 |

5. Delivery of plasmid DNA and siRNA to the prostate via the bladder.

ICR mice were anesthetized with 1-2% isoflurane and a midline incision was made extending from the pubis to the mid-abdomen. Retractors were positioned to expose the bladder and male reproductive organs. Curved vascular clamps were placed on the base of the bladder and the base of the seminal vesicles. Micro vascular clamps were also placed on the right and left ureters, the right and left deferent ducts and the urethral opening. A 30-gauge blunt needle catheter was inserted into the base of the bladder below the vascular clamp. The catheter was connected to a syringe pump and 50 µg pMIR48+4 µg pMIR122 plasmid DNA+25 µg GL3-153 siRNA or 25 µg EGFP-64 siRNA in 0.5 ml Ringer's was injected at a rate of 3 ml/min. Two min after the injection the catheter was removed and the needle hole sealed with a hemostatic sponge. All clamps were removed and the abdominal wall was closed in two layers with 4-0 suture. The results show efficient delivery of plasmid DNA and siRNA to the prostate. Delivery of the plasmid results in expression of genes encoded on the plasmid. Delivery of the siRNA results in specific inhibition of gene expression.

TABLE 5

Intravascular delivery of plasmid DNA and siRNA to prostate

| SiRNA | Luciferase Activity | | |
|---|---|---|---|
| | firefly | Renilla | firefly/Renilla |
| 25 µg GL3-153 | 4330 | 16190 | 0.27 |
| | 120720 | 287590 | 0.42 |
| | 34120 | 41320 | 0.83 |
| | 2730 | 7890 | 0.35 |
| | | mean | 0.46 |
| 25 µg EGFP-64 | 239070 | 22310 | 10.72 |
| | 43760 | 9490 | 4.61 |
| | 561210 | 49280 | 11.39 |
| | 371810 | 52830 | 7.04 |
| | | mean | 8.44 |

6. Delivery of plasmid DNA and siRNA to the prostate via the bladder.

ICR mice were anesthetized with 1-2% isoflurane and a midline incision was made extending from the pubis to the mid-abdomen. Retractors were positioned to expose the bladder and male reproductive organs. Curved vascular clamps were placed on the base of the bladder and the base of the seminal vesicles. Micro vascular clamps were also placed on the right and left ureters, the right and left deferent ducts and the urethral opening. A 30-gauge blunt needle catheter was inserted into the base of the bladder below the vascular clamp. The catheter was connected to a syringe pump and 50 µl pMIR48+10 µg pMIR122 plasmid DNA±25 µg GL3-153 siRNA in 250 µl ml Ringer's was injected at a rate of 3 ml/min. Two min after the injection the catheter was removed and the needle hole sealed with a hemostatic sponge. All clamps were removed and the abdominal wall was closed in two layers with 4-0 suture. The results show efficient delivery of plasmid DNA and siRNA to the prostate. Delivery of the plasmid results in expression of genes encoded o the plasmid. Delivery of the siRNA results in specific inhibition of gene expression.

TABLE 6

Intravascular delivery of plasmid DNA and siRNA to prostate

| SiRNA | Luciferase Activity | | |
|---|---|---|---|
| | firefly | Renilla | firefly/Renilla |
| 25 µg GL3-153 | 1333300 | 1018050 | 1.31 |
| | 685450 | 512940 | 1.34 |
| | 1039545 | 1428185 | 0.73 |
| | | mean | 1.12 |

TABLE 6-continued

Intravascular delivery of plasmid DNA and siRNA to prostate

| SiRNA | Luciferase Activity | | |
|---|---|---|---|
| | firefly | Renilla | firefly/Renilla |
| none | 3896995 | 318030 | 12.3 |
| | 5348875 | 139560 | 38.3 |
| | 2835410 | 189300 | 15.0 |
| | | mean | 21.9 |

7. Intravascular delivery of polynucleotides to the prostate in rat.

100 micrograms of pCILuc was diluted into 30 ml Ringer's solution and injected into the tail vein of 480 gram Harlan Sprague Dawley rat. The entire volume was delivered within 15 seconds. No clamps were applied to specifically target the volume to the prostate. 24 hours after injection various organs were harvested and assayed for luciferase expression. The results demonstrate that the process is effective for delivery in rat as well as mouse.

TABLE 7

Intravascular delivery of DNA to prostate in rat.

| Organ | Total Relative Light Units per organ |
|---|---|
| Liver | 30,200,000,000 |
| Spleen | 14,800,000 |
| Lung | 23,600,000 |
| Heart | 5,540,000 |
| Kidney | 19,700,000 |
| Prostate | 3,490,000 |
| Skeletal Muscle (quadriceps) | 7,670,000 |

8. Influence of injection solution and vessel occlusion on intravascular delivery of plasmid DNA to liver via injection in the portal vein:

The livers of ~25 g, 6-week old mice were exposed through a ventral midline incision. A solution containing 100 µg pBS.CMVLux plasmid in 1 ml injection solution was manually injected over approximately 30 sec into the portal vein using a 30-gauge, ½' needle. The pBS.CMVLux contains the luciferase gene expressed from the human immediate early cytomegalovirus (CMV) promoter. In some animals, a 5×1 mm, Kleinert-Kutz microvessel clip (Edward Weck, Inc., Research Triangle Park, N.C.) was applied during the injection at the junction of the hepatic vein and caudal vena cava. The clamps were applied prior to injecting the solution and remained in place for 2 min after the injection. Anesthesia was obtained from intramuscular injections of 1000 µg of ketamine-HCl (Parke-Davis, Morris Plains, N.J.) in 1 ml of normal saline and methoxyflurane (Pitman-Moore, Mudelein, Ill. USA) which was administered by inhalation as needed. was purchased from Sigma. Heparin was purchased from LyphoMed (Chicago, Ill.). Two days after injection the livers (average weight of 1.5 g) were harvested, placed into lysis buffer (0.1% Triton X-100, 0.1 M K-phosphate, 1 mM DTT pH 7.8) and homogenized. Samples were then assayed for luciferase activity.

A hypertonic injection solution containing 20% mannitol increased delivery of plasmid DNA to the liver as evidenced by increased luciferase activity. Occlusion of the hepatic vein to transiently prevent fluid flow away from the liver also resulted in increased delivery of plasmid DNA to the liver as evidenced by increased luciferase activity. Inclusion of heparin in the injection solution to prevent microvascular thrombosis further increased delivery of polynucleotides to the liver.

TABLE 8

Effect of injection solution and occlusion on delivery of polynucleotides to the liver via intraportal injection.

| Solution | clamp | Luciferase (total ng/liver) | Number of animals |
|---|---|---|---|
| normal saline | no | 0.4 | 6 |
| 20% mannitol + saline | no | 4.8 | 3 |
| 20% mannitol + saline | yes | 14.6 | 9 |
| 2.5 U/ml heparin in saline | yes | 11.8 | 4 |
| 2.5 U/ml heparin in 15% mannitol in saline | yes | 120.3 | 12 |

9. Effect of injection rate on delivery of polynucleotides to liver in mouse via intraportal injection.

Injections were performed as above except that the rate of injection was varied. The injection solution contained 2.5 U/ml heparin/15% mannital in saline and clamps were used. The times over which the injections were done were varied from 30-120 sec. Delivery was best using an injection time of 30 sec (2 ml/min). Less delivery was observed using injection rates of 1 ml/min and 0.5 ml/min.

TABLE 9

Effect of injection rate on delivery of polynucleotide to liver via intraportal administration.

| | Total luciferase/Liver (ng/Liver/mouse) | | |
|---|---|---|---|
| | 30 sec | 1 min | 2 min |
| Mean | 1,662 | 114 | 18 |

10. Effect of injection volume on delivery of polynucleotides to liver in mouse via intraportal injection.

Injections were performed as above except that the volume of injection was varied. The injection solution contained 2.5 U/ml heparin/15% mannital in saline and clamps were used. Injections were performed in 30 sec. Luciferase expression decreased 70-fold whein the injection volume was reduce to 0.5 ml.

TABLE 10

Effect of injection volume on delivery of polynucleotide to liver via intraportal administration.

| | Total luciferase/Liver (ng/Liver/mouse) | |
|---|---|---|
| | 0.5 | 1 ml |
| Mean | 2.3 | 147.9 |

11. Effect of a pharmaceutical on expression of luciferase in liver following intraportal delivery of a luciferase expression plasmid.

Injections were performed as above using an injection solution contained 2.5 U/ml heparin/15% mannital in saline and occluding the hepatic vein. However, some animals received daily subcutaneous injections of 1 mg/kg of dexamethasone (Elkins-Sinn, Cherry Hill, N.J.) starting one day prior to surgery. Animals that had been injected with daily injections of dexamethasone starting the day prior to plasmid injection exhibited three-fold greater luciferase expression than those aminal that did no receive dexamethasone. The dexamethasone likely stimulates the CMV promoter and thereby directly increases expression of luciferase by stimulating transcription of the luciferase messenger RNA. The use of dexamethasone demonstrates that using a readily available pharmaceutical, the levels of expression can be substantially increased and regulated.

TABLE 11

Effect of dexamethasone on luciferase expression in liver following intravascular delivery of DNA.

| | Total luciferase/liver (ng/Liver/mouse) | |
|---|---|---|
| | NO Dexamethasone | WITH Dexamethasone |
| Mean | 120.3 | 399.8 |

12. Delivery of polynucleotides to live via injection into afferent and efferent vessels.

The previous examples involved injections into an afferent blood vessels of the liver, the portal vein. In the liver, the hepatic vein is an efferent blood vessel since it normally carries blood away from the liver into the inferior vena cava. 100 µg of pCILuc (an improved luciferase expression vector) in 1 ml of normal saline solution plus 15% mannitol and 2.5 units/ml heparin was injected over 30 seconds into hepatic vein via the inferior vena cava. Since it was difficult to directly inject the hepatic vein in rodents, the injections were directed into the inferior cava which was clamped in two locations; proximal and distal (i.e. downstream and upstream) to the entry of the hepatic vein into the inferior vena cava. Specifically, the downstream inferior vena cava clamp was placed between the diaphragm and the entry point of the hepatic vein. The upstream inferior vena cava clamp was placed just downstream of the entry point of the renal veins. Therefore, the 1 ml of the injection fluid largely entered the hepatic vein and the liver. In some of the animals that received retrograde injections into the inferior vena cava, the hepatic artery, mesenteric artery, and portal vein were clamped (occluded). Specifically, the order of placing the clamps were as follows: first on hepatic artery, then portal vein, then downstream vena cava, and then upstream vena cava. The clamps were left in place for an additional 2 min from the time that the last clamp (upstream vena cava clamp) was placed. Intraportal injections were performed as above. Some of the mice also received daily subcutaneous injections of 1 mg/kg of dexamethasone starting one day prior to surgery. Two days after the injections, the luciferase activity was measured as above.

A. Injection into hepatic vein with portal vein and hepatic artery occlusion in animals receiving dexamethasone.
Mean=29,357.6 ng luciferase B. Injection into hepatic vein without clamps in animals not receiving dexamethasone.
Mean=3,285.9 ng luciferase C. Injection into portal vein with hepatic vein occlusion in animals receiving dexamethasone.
Mean=3,818.5 ng luciferase Example 13: Timecourse of Muscle Expression After Intravascular Injection in Rats:

Muscle luciferase expression was measured at several time points following intravascular delivery of the luciferase gene under control of either the CMV promoter (pCI-Luc+) or MCK promoter (pMI-Luc+)into: a) untreated rats, b) rats continuously immunosuppressed (treated with 2.5 mg/kg of FK506 orally and 1 mg/kg dexamethasone subcutaneously one day prior to, one hour prior to and every day thereafter with FK506) or c) transiently immunosuppressed (treated with 10 mg/kg of FK506 orally and 1 mg/kg dexamethasone subcutaneously one day prior to, one hour prior to and one day after intraarterial delivery of pDNA) (Table 12). In untreated rats, luciferase expression was lost after 7 days from the CMV promoter or after 21 days from the MCK promoter. In either pCI-Luc+ or pMI-Luc+ injected rats, anti-luciferase antibodies were detected using ELISA by day 21 and were present at higher levels at day 56 and 70 after and 70 after intravascular pDNA delivery (data not shown).

TABLE 12

Effect of immunosuppression on expression of polynucleotides delivered to rat skeletal muscle cells in vivo.

| | Luciferase Expression (ng/g muscle) | | |
|---|---|---|---|
| Days After Injection | No Treatment | Transient Immunnosuppression | Continuous Immuno-suppression |
| pCI-Luc+ expression plasmid | | | |
| 2 | 990.9 | | |
| 7 | 492.6 | | |
| 21 | 22.1 | | |
| 30 | 10.3 | 672.0 | 1212.0 |
| 56 | 0.3 | | |
| 70 | 0.1 | 17.3 | 464.0 |
| pMI-Luc+ expression plasmid | | | |
| 2 | 37.3 | | |
| 7 | 499.9 | | |
| 21 | 286.9 | | |
| 30 | | 1260.0 | |
| 56 | 3.3 | | |
| 70 | 0.3 | 571.0 | 1140.0 |

14. Intravascular delivery of polynucleotides to liver in non-human primate.

Surgical Description: Cynomolgus monkeys (n=6) weighing 2.5 to 3.3 kg and were sedated with ketamine (10-15 mg/kg IM). After sedation, animals were intubated and anesthesia was maintained with 1.0 to 2.0% isoflurane. An intravenous catheter was inserted into the cephalic vein for administering fluids and EKG electrodes were attached to the limbs for monitoring heart rate. The surgical area was prepped and draped for surgery using aseptic technique. A femoral cutdown was performed and a 5 cm segment of the femoral vein was dissected free of connective tissue. The vein was ligated distally and a 6F introducer was inserted into the vein and secured with a vessel tourniquet. A 4F injection catheter was inserted through the introducer and advanced into the inferior vena cava (IVC). An abdominal incision was made extending from just below the xyphoid to the pubis. A retractor was placed inside the abdominal cavity and moist sponges were used to retract and hold the intestines. The infra hepatic IVC was exposed and the exact placement of the injection catheter within the IVC was adjusted so that the tip of the catheter was adjacent to the hepatic vein. A vessel tourniquet was placed loosely around the infra hepatic IVC to prevent backflow during the nucleic acid injection. The supra hepatic IVC was dissected free of connective tissue and ligament attachments. Immediately before the injection, a vascular clamp was placed on supra hepatic IVC and the vessel tourniquet was tightened around the infra hepatic IVC. The IVC remained occluded during the injection and for 2 minutes post injection. The abdominal cavity was closed in 3 layers with 3-0 PDS suture. The catheter was pulled from the femoral vein, the vessel was ligated and the incision was closed in 2 layers with 3-0 PDS suture. Prior to the completion of the surgery, the animal was given buprenorphine (0.005-0.01 mg/kg IM) as an analgesic. Blood samples were collected on days 0, 1, 4, 7, 14 and 21 for measuring reporter gene expression (secreted alkaline phosphatase), liver enzymes and a complete blood count.

Injection description: Two 60 ml syringes were filled with a total volume of 120 ml of injection solution containing 0.9% NaCl, 7.5% mannitol and 10 mg of CMV-SEAP. Syringes were attached to a syringe pump (Harvard Instrument) and connected to the injection catheter via an extension line with a 3-way stopcock. The injection flow rate was set at either 60, 120 or 160 ml/min. In addition to using the syringe pump, hand injections were performed on two animals. The flow rate was continuous during the injection except for one animal that had a preset pause (5 seconds) half way through the injection. During the injection, the entire liver swelled and patchy areas were blanched from the injection solution. In five of the six animals, it was noted that the liver swelled to the point where fluid would begin to leak out the exterior of the liver capsule by the end of the injection.

Reporter Gene Expression: In all the animals in this study, reporter gene expression peaked at day 2. The first animal (animal #1) in this study was a hand injection and resulted in the highest gene expression (day 2=2414 ng/ml SEAP) in this study. This hand injection delivered ~120 ml of solution/minute. Using a syringe pump we found that 60 ml/min (animal #3) and 120 ml/min (animal #2) resulted in a low level of gene expression on day 2 (99 and 71 ng/ml SEAP respectively) but a flow rate of 160 ml/min (animal #5) dramatically improved expression (day 2=1991 ng/ml SEAP). This injection rate was repeated in a second animal (animal #6) but with a preset pause (5 seconds) halfway through the injection to determine if continuous flow was important for high gene expression. The expression in this animal was also high (day 2=985 ng/ml) but lower than the continuous syringe pump injection. In one additional animal, the pump failed during the injection and had to be helped by hand (animal #4). This injection delivered 120 ml in approximately one minute and resulted in a SEAP level of 350 ng/ml on day 2.

The data indicate that the described procedure is effective in delivering polynucleotides to cells in primates, indicating that the procedure should work in humans as well.

TABLE 12

Hepatic Vein Delivery of Nucleic Acid to Primate Liver. Expression of plasmid CMV-SEAP in liver.

| | SEAP expression (ng/ml) day | | | | | |
|---|---|---|---|---|---|---|
| animal | 0 | 1 | 2 | 4 | 7 | 14 | 21 |
| 1 | | 2300.7 | 2414.7 | 1605.1 | 1144.1 | 504.2 | 0.7 |
| 2 | | 70.9 | 70.8 | 43.4 | 18.0 | 3.4 | 1.6 |
| 3 | | 63.9 | 98.8 | 85.5 | 49.5 | 13.4 | 9.2 |
| 4 | | 206.7 | 350.1 | 184.9 | 59.3 | 55.7 | 2.5 |
| 5 | | 1686.1 | 1990.7 | 1737.8 | 831.9 | 371.7 | 155.8 |
| 6 | | 740.9 | 985.1 | 864.4 | 634.6 | 232.5 | 106.7 |

The foregoing is considered as illustrative only of the principles of the invention. Furthermore, since numerous modifications and changes will readily occur to those skilled in the art, it is not desired to limit the invention to the exact construction and operation shown and described. Therefore, all suitable modifications and equivalents fall within the scope of the invention.

We claim:

1. A process for delivering DNA to a prostate cell in a mammal comprising:
   a) inserting a delivery device into a lumen of an afferent or efferent vessel of the prostate;
   b) injecting a solution containing the DNA into the lumen of the vessel;
   c) increasing permeability of the vessel to the DNA;
   d) delivering the DNA to the prostate cell outside of the vessel; and,
   e) expressing the DNA.

2. The process of claim 1 wherein fluid flow out of the prostate tissue is impeded by occlusion of at least one vessel.

3. The process of claim 1 wherein the vessel consists of a blood vessel.

4. The process of claim 3 wherein the blood vessel consists of a vein.

5. The process of claim 3 wherein the blood vessel consists of an artery.

6. The process of claim 4 wherein the vein is selected from the list consisting of: prostatic venous plexus, prostatic vein, tributaries of the deep dorsal vein of the penis, dorsal vein of the penis, internal iliac vein, and vesical venous plexus, and their tributaries.

7. The process of claim 5 wherein the artery is selected from the list consisting of: inferior vesical artery, internal iliac artery, prostatic artery, internal pudic artery, hemorrhoidal artery, and rectal artery, and their tributaries.

8. The process of claim 1 wherein expression of the DNA induces an immune response.

9. The process of claim 1 wherein the DNA is associated with a transfection agent.

10. The process of claim 1 wherein the solution contains a compound that increases vascular permeability.

11. The process of claim 1 wherein expression of the DNA alters the endogenous properties of the cell.

12. The process of claim 1 wherein the mammal has benign prostatic hyperplasia.

13. The process of claim 1 wherein the mammal has prostate cancer.

* * * * *